(12) United States Patent
Al-Ali

(10) Patent No.: US 7,910,875 B2
(45) Date of Patent: Mar. 22, 2011

(54) SYSTEMS AND METHODS FOR INDICATING AN AMOUNT OF USE OF A SENSOR

(75) Inventor: Ammar Al-Ali, Tustin, CA (US)

(73) Assignee: Masimo Corporation, Irvine, CA (US)

(*) Notice: Subject to any disclaimer, the term of this patent is extended or adjusted under 35 U.S.C. 154(b) by 0 days.

(21) Appl. No.: 11/714,303

(22) Filed: Mar. 6, 2007

(65) Prior Publication Data
US 2007/0156034 A1 Jul. 5, 2007

Related U.S. Application Data

(63) Continuation of application No. 11/311,212, filed on Dec. 19, 2005, now Pat. No. 7,186,966, which is a continuation of application No. 11/065,994, filed on Feb. 24, 2005, now Pat. No. 6,979,812, which is a continuation of application No. 10/357,531, filed on Feb. 3, 2003, now Pat. No. 6,861,639, which is a continuation of application No. 09/502,032, filed on Feb. 10, 2000, now Pat. No. 6,515,273, which is a continuation-in-part of application No. 09/420,544, filed on Oct. 19, 1999, now Pat. No. 6,580,086.

(60) Provisional application No. 60/150,922, filed on Aug. 26, 1999.

(51) Int. Cl.
*H01J 40/14* (2006.01)

(52) U.S. Cl. .................. 250/214 R; 250/214.1

(58) Field of Classification Search ............ 250/214 R, 250/214.1, 461.2, 338.5, 221; 356/39, 41; 600/300, 344
See application file for complete search history.

(56) References Cited

U.S. PATENT DOCUMENTS

| | | | |
|---|---|---|---|
| 4,621,643 | A | 11/1986 | New, Jr. et al. |
| 4,685,464 | A | 8/1987 | Goldberger et al. |
| 4,960,128 | A | 10/1990 | Gordon et al. |
| 4,964,408 | A | 10/1990 | Hink et al. |
| RE33,643 | E | 7/1991 | Isaacson et al. |
| 5,041,187 | A | 8/1991 | Hink et al. |
| 5,069,213 | A | 12/1991 | Polczynski |
| 5,090,410 | A | 2/1992 | Saper et al. |
| 5,163,438 | A | 11/1992 | Gordon et al. |

(Continued)

FOREIGN PATENT DOCUMENTS

EP 0262 779 A1 4/1988

(Continued)

OTHER PUBLICATIONS http://www.masimo.com/systemo.htm, "System Overview & Performance," 2 pages reviewed on Sep. 17, 1999.

(Continued)

*Primary Examiner* — Que T Le
(74) *Attorney, Agent, or Firm* — Knobbe, Martens, Olson & Bear LLP

(57) ABSTRACT

Aspects of the present disclosure include systems and methods for indicating an amount of use of a pulse oximetry sensor. According to one embodiment, the system includes an oximeter that monitors the amount of use for a given sensor. The oximeter and/or the sensor may advantageously include a visual alarm, an audio alarm, a vibrational alarm, a power down function, or the like, which can be activated when a predetermined amount of use has expired. According to another embodiment, the system includes a sensor having a memory device storing a unique identifier.

10 Claims, 8 Drawing Sheets

U.S. PATENT DOCUMENTS

| | | | |
|---|---|---|---|
| 5,170,786 A | 12/1992 | Thomas et al. | |
| 5,188,098 A | 2/1993 | Hoffman et al. | |
| 5,247,931 A | 9/1993 | Norwood | |
| 5,309,908 A | 5/1994 | Friedman et al. | |
| 5,313,940 A | 5/1994 | Fuse et al. | |
| 5,319,355 A | 6/1994 | Russek | |
| 5,337,744 A | 8/1994 | Branigan | |
| 5,431,170 A | 7/1995 | Mathews | |
| 5,438,986 A | 8/1995 | Disch et al. | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,588,427 A | 12/1996 | Tien | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,660,567 A | 8/1997 | Nierlich et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,807,248 A | 9/1998 | Mills | |
| 5,810,724 A | 9/1998 | Gronvall | |
| 5,810,734 A | 9/1998 | Caro et al. | |
| 5,817,010 A | 10/1998 | Hibl | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,133 A | 7/1999 | Taylor et al. | |
| 5,919,134 A | 7/1999 | Diab | |
| 5,934,925 A | 8/1999 | Tobler et al. | |
| 5,939,609 A | 8/1999 | Knapp et al. | |
| 5,940,182 A | 8/1999 | Lepper, Jr. et al. | |
| 5,991,355 A | 11/1999 | Dahlke | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,308,089 B1 * | 10/2001 | von der Ruhr et al. | 600/338 |
| 6,334,065 B1 | 12/2001 | Al-Ali et al. | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,725,075 B2 | 4/2004 | Al-Ali | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Al et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,241,270 B2 * | 7/2007 | Horzewski et al. | 601/2 |
| 2001/0045532 A1 | 11/2001 | Schulz et al. | |

FOREIGN PATENT DOCUMENTS

| | | |
|---|---|---|
| EP | 0 481 612 A1 | 4/1992 |
| EP | 0 745 348 A1 | 12/1996 |

| | | |
|---|---|---|
| EP | 0 832 598 A2 | 9/1997 |
| JP | 02-191434 | 7/1990 |
| WO | WO 97/23159 | 7/1997 |

OTHER PUBLICATIONS http://www.masimo.com/pandt.htm, "Products & Technology," 1 page reviewed on Sep. 17, 1999.

http://www.masimo.com/cables.htm, "Patient Cables," 1 page reviewed on Sep. 17, 1999.

http://www.masimo.com/adt.htm, "Inop-adt—Adult Disposable Digit Sensor," 1 page reviewed on Sep. 17, 1999.

http://www.mrequipment.com/products/pulse_oximetry.htm, "MR Equipment Magnetic Resonance Equipment Corporation, Pulse_Oximetry in MRI Model 3500 Pulse Oximeter," 2 pages reviewed on Sep. 17, 1999.

http://www.mrequipment.com/products/oximetry_patient_mntrg.htm, "MR Equipment Magnetic Resonance Equipment Corporation, MR-Compatible High-Performance Optical Fiber Sensors, Pulse Oximetry Sensors for MRI Fiber Optic Sensors for use with MR-Compatible Pulse Oximeter," 2 pages reviewed on Sep. 17, 1999.

Article entitled "Masimo Corporation, Discrete Saturation Transform Example," reviewed on Sep. 17, 1999.

http://www.dalsemi.com, "Dallas Semiconductor," page 1 only, reviewed on Jan. 12, 2000.

http://www.dalsemi.com/Prod_info/AudoID/index.html, "Dallas Semiconductor Automatic Information Overview," 10 pages reviewed on Jan. 12, 2000.

Awtrey, "Sensors: The Journal of Applied Sensing Technology, Transmitting Data and Power over One-Wire Bus," 4 pages, Feb. 1997.

Dallas Semiconductor, Application Note 30, "Recording Power Cycling Information Using the DS1602/DS1603," pp. 7-9, 1993.

Dallas Semiconductor, "DS 1602 Elapsed Time Counter," pp. 468-476, 1993.

Dallas Semiconductor, "DS 1603 Elapsed Time Counter Modual," pp. 477-484, 1993.

Dallas Semiconductor "DS2401 Silicon Serial Number," 10 pages, Oct. 21, 1999.

Dallas Semiconductor "DS2502 1Kbit Add-Only Memory," pp. 149-169, 1993.

Patent Abstract of Japan; Publication No. 10314149; Publication Date: Feb. 12, 1998; U.S. Appl. No. 09/129,922; Application Date: May 20, 1997; Inventor: Suzuki Hiroaki; Title Probe Exchangeable Electric Measurement Device, Probe Management Method and Pulse Oximeter.

Patent Abstract of Japan; Publication No. 1053662; Publication Date: Feb. 26, 1999.

Patent Abstract of Japan; Publication No. 02017462; Publication Date: Jan. 22, 1990.

Patent Abstract of Japan; Publication No. 11185193; Publication Date: Jul. 9, 1999.

PCT International Search Report, App. No. PCT/US 00/22849, App. Date: Aug. 21, 2000, 4 pages.

PCT International Search Report, App. No. PCT/US01/04265, App. Date Feb. 9, 2001, 4 pages.

International publication corresponding to copending U.S. Appl. No. 09/420,544, filed Oct. 19, 1999.

Office Action dated Sep. 19, 2007 from Related Application No. 06 006 843.4-2305.

Co-pending U.S. Appl. No. 11/580,214, filed Oct. 16, 2006, 33 pages.

* cited by examiner

US 7,910,875 B2

SYSTEMS AND METHODS FOR INDICATING AN AMOUNT OF USE OF A SENSOR

REFERENCE TO RELATED APPLICATION

The present application claims priority benefit under 35 U.S.C. §120 to and is a continuation of U.S. patent application Ser. No. 11/311,212, filed Dec. 19, 2005 now U.S. Pat. No. 7,186,966, entitled "Amount of Use Tracking Device and Method for Medical Product," which is a continuation of U.S. patent application Ser. No. 11/065,994, filed Feb. 24, 2005, entitled "Systems and Methods for Indicating an Amount of Use of a Sensor," now U.S. Pat. No. 6,979,812, which is a continuation of U.S. patent application Ser. No. 10/357,531, filed Feb. 3, 2003, entitled "Systems and Methods for Indicating an Amount of Use of a Sensor," now U.S. Pat. No. 6,861,639, which is a continuation of U.S. patent application Ser. No. 09/502,032, filed Feb. 10, 2000, entitled "A System for Indicating the Expiration of the Useful Operating Life of a Pulse Oximetry Sensor," now U.S. Pat. No. 6,515,273, which is a continuation-in-part of U.S. patent application Ser. No. 09/420,544, filed Oct. 19, 1999, entitled "Shielded Optical Probe and Method," now U.S. Pat. No. 6,580,086, which claimed a priority benefit under 35 U.S.C. §119(e) to U.S. Provisional Patent Application Ser. No. 60/150,922, filed Aug. 26, 1999, by the same title. The present application incorporates the foregoing disclosures herein by reference.

BACKGROUND OF THE INVENTION

1. Field of the Invention

The present invention in general relates to sensors for measuring oxygen content in the blood, and, in particular, relates to an apparatus and method for monitoring the life of a pulse oximetry sensor.

2. Background

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed pulse oximetry, a noninvasive procedure for measuring the oxygen saturation of the blood. A pulse oximeter interprets signals from a sensor attached to a patient in order to determine that patient's blood oxygen saturation.

A conventional pulse oximetry sensor has a red emitter, an infrared emitter, and a photodiode detector. The sensor is typically attached to a patient's finger, earlobe, or foot. For a finger, the sensor is configured so that the emitters project light from one side of the finger, through the outer tissue of the finger, and into the blood vessels and capillaries contained inside. The photodiode is positioned at the opposite side of the finger to detect the emitted light as it emerges from the outer tissues of the finger. The photodiode generates a signal based on the emitted light and relays that signal to the pulse oximeter. The pulse oximeter determines blood oxygen saturation by computing the differential absorption by the arterial blood of the two wavelengths (red and infrared) emitted by the sensor.

The foregoing conventional sensor is typically detachable from the oximeter to allow for periodic replacement. Periodic replacement is advantageous for a wide variety of reasons. For example, the sensor can become soiled, thereby possibly inhibiting sensor sensitivity or causing cross-patient contamination. Furthermore, the electronic circuitry in the sensor can become damaged, thereby causing sensor failure or inaccurate results. Moreover, the securing mechanism for the sensor, such as an adhesive substrate, can begin to fail, thereby improperly positioning the sensor in proximity to a measurement site and providing inaccurate data. Accordingly, periodic replacement of the sensor is an important aspect of maintaining a sterile, highly sensitive, accurate pulse oximetry system.

However, a conventional pulse oximetry sensor is wholly reliant on an operator for timely replacement of soiled, damaged, or otherwise overused sensors. This approach is problematic not only from the standpoint of operator mistake or negligence, but also from the perspective of deliberate misuse for cost saving or other purposes.

Based on the foregoing, significant drawbacks exist in the reliance on the operator for the periodic replacement of conventional pulse oximetry sensors. Accordingly, a need exists for a pulse oximetry sensor having the ability to monitor its own usable life.

SUMMARY OF THE INVENTION

Accordingly, one aspect of the present invention is to provide an inexpensive, highly accurate sensor life monitoring system for monitoring the useful and safe life of a pulse oximetry sensor. According to one embodiment, the sensor life monitoring system includes a timer and a sensor life indicator. According to another embodiment, the timer includes a divide-by-n counter and a non-volatile RAM, while the sensor life indicator includes at least one LED or incandescent bulb.

Therefore, one aspect of the present invention is a pulse oximetry sensor comprising a drive connection carrying a drive signal, wherein the drive signal has pulses. The pulse oximetry sensor further comprises a timer connected to the drive connection and configured to generate a timer output signal after a predetermined number of pulses are generated in the drive signal; and a sensor life indicator connected to the timer output signal and configured to provide an indication when the timer output signal is generated. The pulse oximetry sensor further comprises an LED network connected to the drive connection and configured to project light through a measurement site when pulsed by the drive signal; and a photodetector configured to detect the projected light and output a signal representative of constituents or characteristics of the measurement site.

Another aspect of the present invention is a sensor life monitoring system comprising a timer connected to a sensor drive signal; and a sensor life indicator connected to the timer such that the sensor life indicator is configured to indicate the expiration of the useful or safe life of a pulse oximetry sensor.

Another aspect of the present invention is a pulse oximetry system that comprises a pulse oximeter; a sensor connected to the pulse oximeter; and a sensor life monitor connected to the sensor and configured to monitor the useful and safe life of the sensor.

Another aspect of the present invention is a method of manufacturing a sensor. The method comprises connecting a timer to one of a sensor input and a sensor output; and connecting an indicator to the timer such that when the timer expires, the indicator is activated.

Another aspect of the present invention is a method for monitoring the life of an oximetry sensor. The method comprises monitoring a parameter responsive to repeated use of a sensor. When the parameter indicates that the sensor has expired, the method generates an expiration indication.

Another aspect of the present invention is an oximetry sensor life indicator that comprises a non-volatile counter connected to receive a drive signal having a plurality of transitions where the counter changes a count value in response to the transitions. The oximetry sensor life indicator further includes a sensible indicia connected to the counter, where the sensible indicia has a first state, and a second state and the sensible indicia changes from the first state to the second state to indicate the end of life of the oximetry sensor when the count value in the counter reaches a predetermined value.

Another aspect of the present invention is an oximetry system comprising an oximeter; a sensor attached to the oximeter through a cable; a timer connected to at least one of a sensor drive signal and a sensor return signal; and a sensor life indicator connected to the timer.

Another aspect of the present invention is an oximetry system comprising a sensor having a timer, wherein the timer produces a sensor expiration signal. An oximeter is connected to the sensor and is configured to receive the sensor expiration signal from the timer.

Another aspect of the present invention is an oximetry system comprising a sensor having a reset indicator. An oximeter is connected to the sensor and is configured to monitor whether the reset indicator has been set.

Another aspect of the present invention is a pulse oximetry system comprising a pulse oximeter and a sensor connected to the pulse oximeter. The sensor is adapted to measure a physiological parameter. The pulse oximetry system also comprises a memory device connected to the sensor and adapted to measure the useful life of the sensor.

Another aspect of the present invention is a pulse oximetry system comprising a sensor having an emitter, a detector, and a memory device storing a characteristic of the sensor. The pulse oximetry system also comprises a pulse oximeter connected to the sensor and adapted to read the characteristic of the sensor and the output of the detector. The pulse oximetry system also comprises a database connected to the pulse oximeter and adapted to store the characteristic along with a longevity measurement corresponding to the sensor.

For the purposes of summarizing the invention, certain aspects, advantages, and novel features of the invention have been described. Of course, it is to be understood that not necessarily all such advantages may be achieved in accordance with any particular embodiment of the invention. Thus, the invention may be embodied or carried out in a manner that achieves or optimizes one advantage or a group of advantages, as taught herein, without necessarily achieving other advantages as may be taught or suggested herein.

Other aspects and advantages of the invention will be apparent from the detailed description below and the appended claims.

BRIEF DESCRIPTION OF THE DRAWINGS

The present invention is described in more detail below in connection with the attached drawings, which are meant to illustrate and not limit the invention, and in which.

DETAILED DESCRIPTION

The inventions are described in detail below with reference to the figures, wherein like elements are referenced with like numerals throughout.

Figure 1:
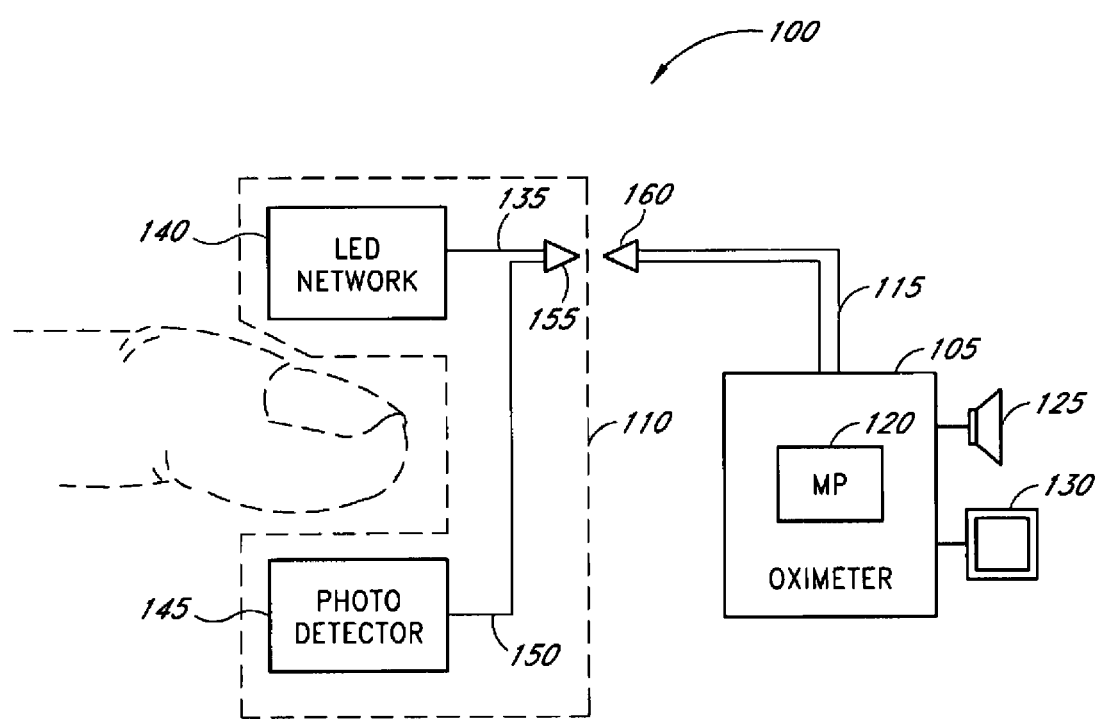
FIG. 1 illustrates a block diagram of a typical oximetry system.

FIG. 1 illustrates a block diagram of a typical oximetry system 100 used to determine arterial oxygen saturation. The oximetry system 100 includes an oximeter 105 and a sensor 110 connected to the oximeter 105 via a patient cable 115. The oximeter 105 includes a microprocessor (μp) 120, a speaker 125 and a display 130. The sensor 110 includes a drive connection 135 connected to at least one LED network 140, a photo detector 145 connected to a return signal connection 150, and a cable connector 155 housing one end of each of the drive connection 135 and the return signal connection 150. As mentioned, the sensor 110 attaches to the oximeter 105 via the patient cable 115. The patient cable 115 includes a sensor connector 160 for electrically mating with the cable connector 155 of the sensor 110.

As previously mentioned, the typical oximetry system 100 produces a drive signal and transmits the drive signal through the patient cable 115 and the drive connection 135 to the LED network 140 such that light energy is transmitted from the LED network 140 through tissue. The photo detector 145 senses the light energy, which has now been attenuated by the blood in tissue, and sends a representative signal of the light energy back to the oximeter 105 through the return signal connection 150 and the patient cable 115. The oximeter 105 analyzes the representative signal from the photo detector 145 to determine constituence and characteristics of the blood in the tissue.

The sensor 110 typically includes the foregoing electronic circuitry and an attachment mechanism formed to secure the electronic circuitry to a measurement site. The sensor 110 may be disposable, wherein the attachment mechanism is likely formed from an adhesive structure. Moreover, the sensor 110 may be reusable, wherein the attachment mechanism is likely formed from a clip-on structure. Also, the sensor 110 may be a combination of the disposable and reusable type sensors, wherein a disposable attachment mechanism removably attaches the electronic circuitry such that the electronic circuitry is reusable. Furthermore, the sensor 110 may include an information element electrically connected to the LED network 140. Such an information element advantageously provides quality control, security, and identification functions.

An example of the combination sensor having an information element distributed in the disposable attachment mechanism is described in U.S. patent application Ser. No. 09/456,666, filed on Dec. 9, 1999, titled, "Resposable Pulse Oximetry Sensor," assigned to the assignee of the current application, and incorporated by reference herein.

Figure 2:
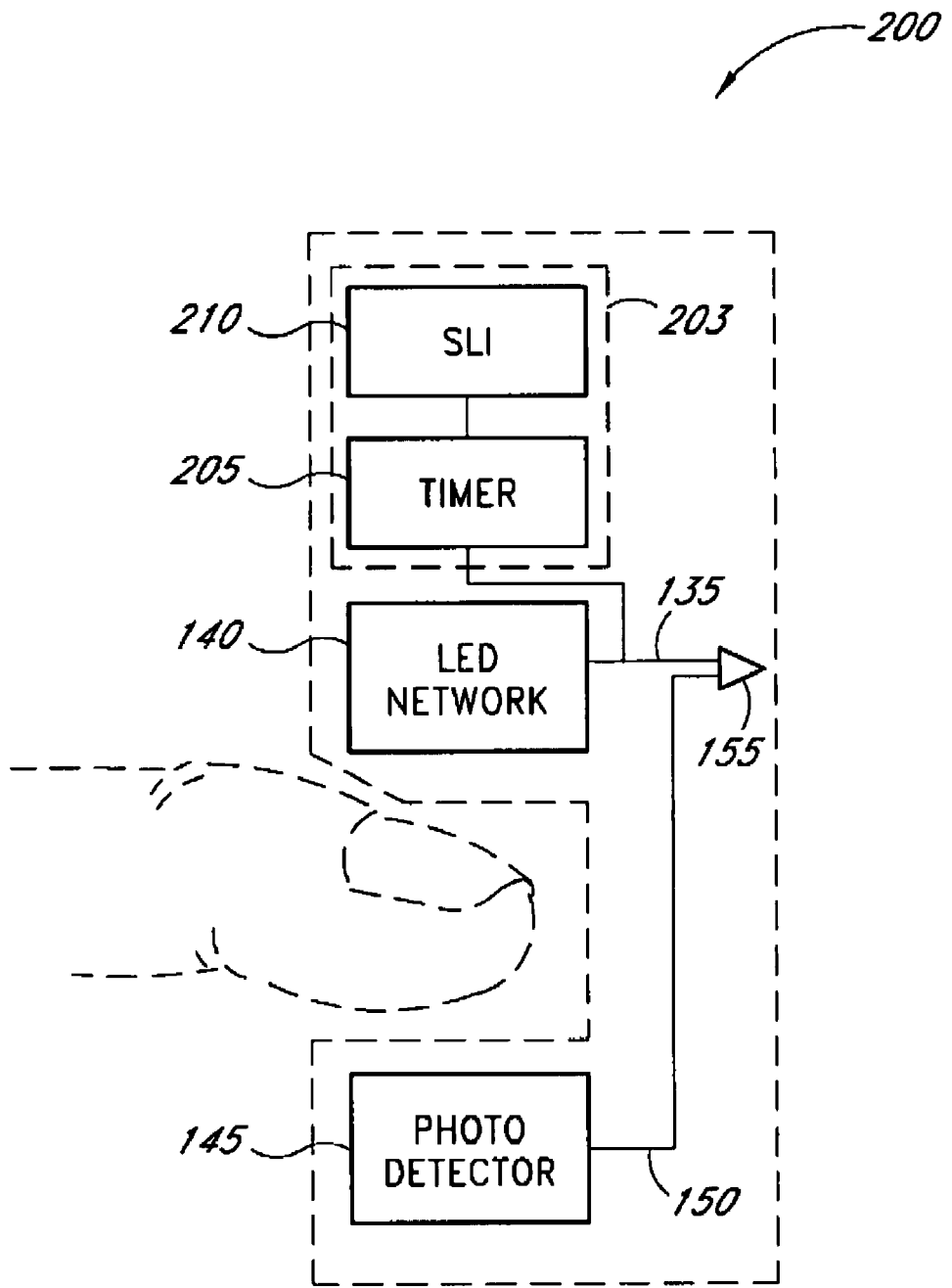
FIG. 2 illustrates a block diagram of a sensor life monitoring system according to an embodiment of the invention.

FIG. 2 illustrates a block diagram of a pulse oximetry sensor 200, according to an embodiment of the invention. As shown in FIG. 2, the sensor 200 includes a wholly incorporated sensor life monitoring system 203. The sensor life monitoring system 203 includes a timer 205 and a sensor life indicator (SLI) 210. According to this embodiment, the timer 205 is electrically connected to the drive connection 135 such that the timer 205 also receives the drive signal from the oximeter 105. The timer 205 also connects to the sensor life indicator 210.

As the oximeter 105 drives the LED network 140, the timer 205 monitors the number of drive pulses produced and keeps a running count. After the oximeter 105 produces a predetermined number of drive signals, the timer 205 provides a signal to the sensor life indicator 210, such that the sensor life indicator 210 produces an indication that the sensor 200 has expired and should be replaced.

Figure 3:
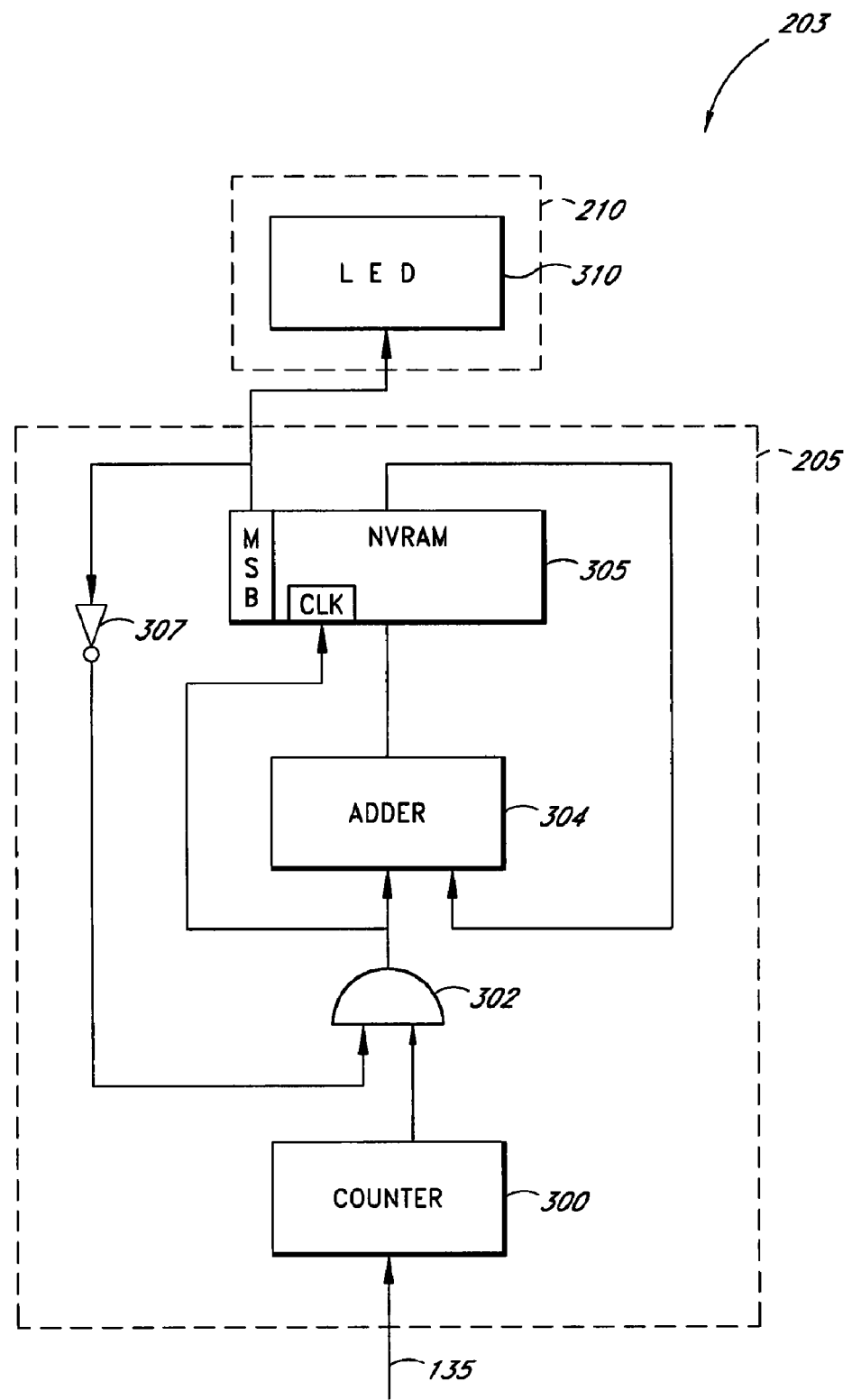
FIG. 3 illustrates a block diagram of the sensor life monitoring system of FIG. 2, according to another embodiment of the invention.

FIG. 3 illustrates a block diagram of an example of the sensor life monitoring system 203 of FIG. 2, according to one embodiment of the invention. As shown in FIG. 3, the timer 205 advantageously comprises a non-volatile counter. One embodiment of the non-volatile counter advantageously comprises a counter 300 having an output that connects to an input of a logic gate 302. An output of the logic gate 302 connects to an adder 304. As used herein, an "adder" can be an arithmetic unit, which may also be implemented as a subtractor or the like. The adder 304 connects to a non-volatile (NV) RAM 305 (A non-volatile RAM does not lose data when the power is turned off or otherwise terminated). An output of the NVRAM 305 reconnects as feedback to the adder 304. Also, an output of the most significant bit (MSB) of the NVRAM 305 connects to both an inverter 307 and the sensor life indicator 210. The inverter 307 connects as feedback to another input of the logic gate 302. Moreover, the output of the logic gate 302 activates or clocks the NVRAM 305.

According to one embodiment, the counter 300 comprises a divide-by-n counter, producing an incremental output count only after n input pulses, or transitions, of the drive signal. Using a divide-by-n counter advantageously reduces the capacity requirements of the NVRAM 305. Furthermore, according to one embodiment, the logic gate 302 is an AND gate, the adder 304 is a plus-one adder. Thus, each time the adder 304 receives an input, it adds one to the current count stored in the NVRAM 305. According to one embodiment, the NVRAM 305 is a seventeen-bit non-volatile memory that clocks, for example, on the trailing edge of the output of the logic gate 302.

According to an embodiment of the invention, the sensor life indicator 210 comprises a sensible indicia, such as visible light. For example, the sensible indicia may advantageously be an LED 310, or the like. Alternatively, the sensible indicia may be audible, vibrational, a power down of the sensor 200 or the oximeter 105, or the like.

The operation of the foregoing timer 205 and sensor life indicator 210 will be disclosed with reference to two differing time frames. The first time frame refers to when a new sensor 200 is initially attached to the oximeter 105 and provided with a drive signal. The second time frame refers to when the sensor 200 has previously been used, and a new drive signal is applied.

First Use of the Sensor 200

According to the foregoing embodiment, the sensor life monitoring system 203 initially functions as follows. The oximeter 105 outputs a drive signal at, for example, one kHz. The counter 300 comprises a divide-by-1000 counter that advantageously produces, for example, an output only after one thousand cycles of the drive signal, or every one second. Furthermore, assuming the count stored in the NVRAM 305 is initially zero, the output of the MSB of the NVRAM 305 is zero. The inverter 307 inverts the output of the MSB such that the logic gate 302 passes the output of the counter 300 to the adder 304. Thus, according to this example, the adder 304 receives a pulse every second from the counter 300. With each pulse, the adder 304 adds one to count stored in the NVRAM 305. Thus, after one second, the adder 304 places a one in the NVRAM 305. After another second, the adder 304 places a two in the NVRAM 305, and so forth until the NVRAM 305 fills to capacity, or the oximeter 105 ceases producing the drive signal. Both events are further discussed as follows.

Subsequent Use of the Sensor 200

When the oximeter 105 sends pulses to a previously used sensor 200, the NVRAM 305 will already have a previous count stored therein. The previous count is loaded into the adder 304 such that as the logic gate 302 outputs the foregoing signal every second, the adder 304 adds one to the previous count. For example, if the previous count were one hour, or 3,600 seconds, the first pulse received by the adder 304 from the counter 300 will store 3,601 in the NVRAM 305. Thus, much like an automobile odometer, the NVRAM 305 stores a running count, or times, the used life of the sensor 200.

When the count stored in the NVRAM 305 reaches capacity (in other words, sets the MSB), the output of the MSB switches. Therefore, the output of the inverter 307 switches such that the logic gate 302 blocks any future signals output from the counter 300 from reaching the adder 304. Moreover, the output of the MSB further activates the LED 310 such that the LED 310 indicates the sensor 200 has expired. This indication by the LED 310 signals the operator to replace the used sensor 200 with a new one. The indication advantageously provides multiple people with the knowledge that the sensor 200 should be changed. For example, doctors, nurses, visitors, and even the patient may perceive the indication that the sensor 200 has expired.

According to the foregoing embodiment where every second that the oximeter 105 sends drive pulses to the sensor 200, the seventeen-bit NVRAM 305 is incremented, the MSB of the NVRAM 305 will set after 131,072 seconds, or, one day, twelve hours, twenty-four minutes and thirty two-seconds. In other words, according to this embodiment, the useful life of the sensor 200 expires after the sensor 200 has received drive pulses for a combined total of the foregoing time.

A skilled artisan will understand that a wide number of differing logic mechanisms may be employed in the foregoing embodiment. For example, employing different sized counters 300 or NVRAMs 305 will adjust the predetermined expiration time. Moreover, the counter 300 may advantageously divide by more than one thousand, thereby further reducing the capacity requirements of the NVRAM 305. Also, the timer 205 may advantageously comprise a non-volatile counter that has internal registers that retain their values when the power is turned off. Such non-volatile counters are available, for example, from Dallas Semiconductor Corporation of Dallas, Tex. These non-volatile counters may include, for example, Dallas Semiconductor's DS1602 or DS1603. In the foregoing embodiments employing a non-volatile counter, the adder 304 and the counter 300 may not be needed.

A skilled artisan will also understand that the sensor 200 may advantageously employ a wide variety of differing timers 205 and differing sensor life indicators 210. Moreover, the choice may advantageously coincide with particular types of the sensor 200. For example, a purely disposable sensor suggests a less costly solution than that of the reusable sensor because of manufacturing costs and the relatively short life of the disposable sensor. On the other hand, the combination sensor may incorporate a more expensive solution into the reusable portion of the electronic circuitry without dramatic cost changes to the disposable portion.

Moreover, a skilled artisan will recognize that the timer 205 may advantageously comprise a capacitor that is charged when the sensor 200 is connected to the oximeter 105. In such case, the capacitor has known discharge characteristics such that the voltage across the capacitor can be used to measure the useful life of the sensor 200. Also, rather than using the pulses of the drive signal, the timer 205 may employ an oscillator configured to trigger at the beginning of sensor use.

Further, the sensor life indicator 210 may include several LEDs of differing colors, such as green and red, to indicate whether the sensor 200 has expired. The sensor life indicator 210 may comprise an incandescent light, an audio or vibrational alarm, a digital or LCD display, or other sensible indicia. Moreover, the sensor life indicator 210 may include a blocking signal for automatically terminating the functionality of the sensor 200. For example, a logic gate may be advantageously added to the drive signal such that the logic gate has the drive signal as an input and has the output of the timer 205 as the another. When the output of the timer 205 is a logic level signaling expiration, the logic gate blocks the drive signal from passing, thus rending the sensor 200 inoperative. The foregoing logic circuit may also be used to block the signal transferred through the return signal connection 150. On the other hand, the blocking signal may also comprise a fuse that once blown, renders the sensor 200 inoperative.

Accordingly, a skilled artisan may perceive a variety of differing devices to measure the longevity of the sensor 200. Furthermore, the type of the sensor 200 may provide guidance on which of the wide variety of devices to use.

Figure 4:
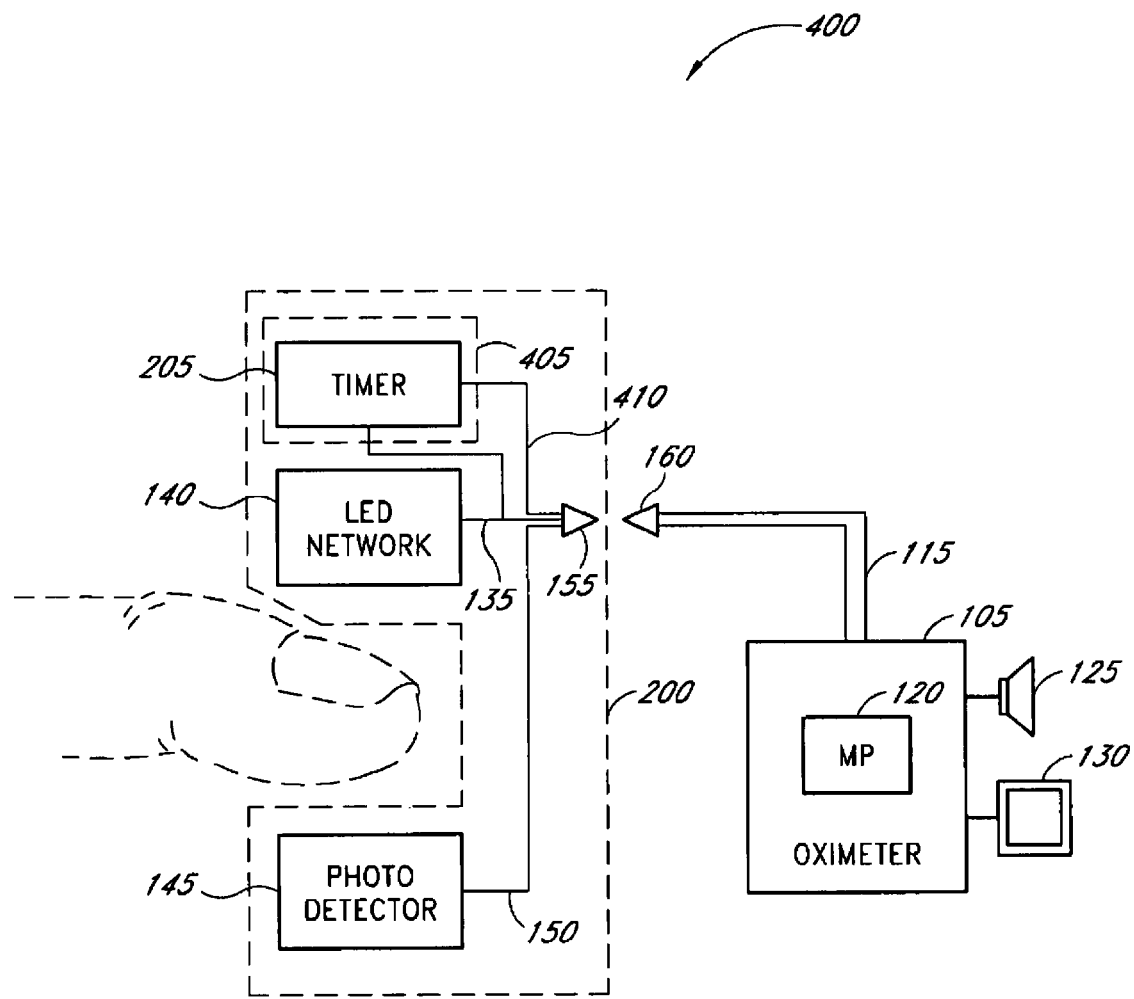
FIG. 4 illustrates a block diagram of an oximetry system having a sensor life monitoring system, according to yet another embodiment of the invention.

FIG. 4 illustrates a block diagram of yet another embodiment of an oximetry system 400 including a sensor life monitoring system 405. According to this embodiment, the sensor life monitoring system 405 employs the timer 205 and a return signal 410 to the oximeter 105. Similar to the foregoing embodiment, the timer 205 connects to the drive connection 135 and uses the pulses of the drive signal to measure the useful and safe life of the sensor 200. In contrast to the foregoing embodiment, the timer 205 then outputs an incremental count of pulses to the oximeter 105 via the return signal 410, the cable connector 155, the sensor connector 160, and the patient cable 115. In this embodiment, the microprocessor 120 of the oximeter 105 receives the incremental count from the timer 205 and compares the incremental count with a predetermined amount. If the count is greater than the predetermined amount, the microprocessor 120 issues an expiration indication of the sensor 200 through the oximeter 105.

A skilled artisan will recognize that the oximeter 105 may issue the expiration indication through a wide variety of devices including, but not limited to, those described in relation to the sensor life indicator 210 of FIGS. 2-3. Moreover, the oximeter 105 may take advantage of the more costly technology already associated therewith. For example, the oximeter 105 may issue the expiration indication by employing an audio alarm through the speaker 125, a visual alarm through the display 130, or a power-down function where the oximeter 105 is inoperable until the sensor 200 is replaced.

Figure 5:
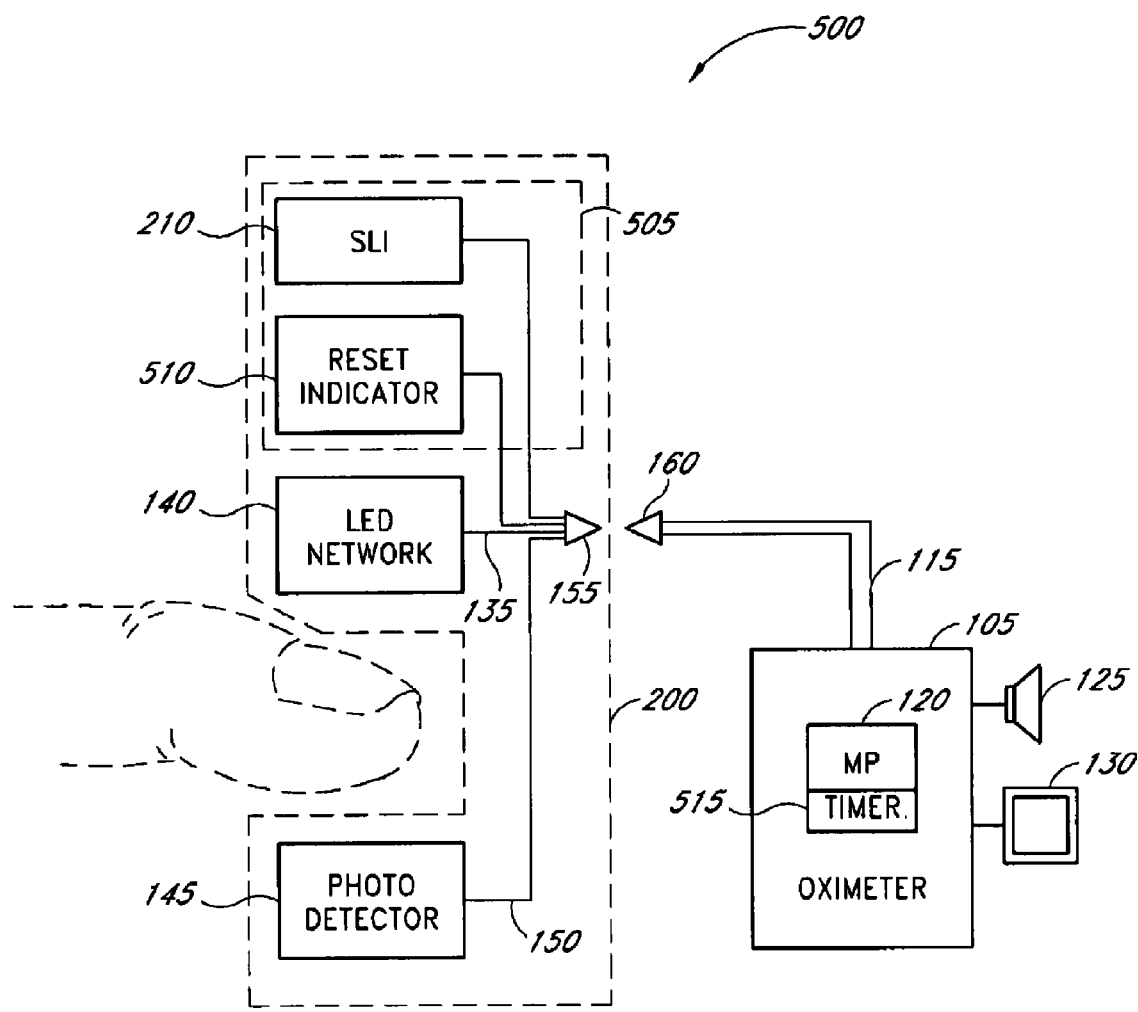
FIG. 5 illustrates a block diagram of an oximetry system having a sensor life monitoring system, according to yet another embodiment of the invention.

FIG. 5 illustrates a block diagram of yet another embodiment of an oximetry system 500 including a sensor life monitoring system 505. According to this embodiment, the sensor life monitoring system 505 employs a reset indicator 510 and the sensor life indicator 210, as an integral part of the sensor 200. The reset indicator 510 and the sensor life indicator 210 connect to the oximeter 105 through the cable connector 155, the sensor connector 160, and the patient cable 115. Also according to this embodiment, the microprocessor 120 includes a timer 515.

According to this embodiment, the microprocessor 120 measures the useful and safe life of the sensor 200. For example, the microprocessor 120 may track the pulses in the drive signal created by the microprocessor 120, or take advantage of a date/time function to measure actual time. Furthermore, the microprocessor 120 employs the reset indicator 510 on the sensor 200 to indicate whether the sensor 200 is newly attached or has previously expired. For example, the reset indicator 510 may comprise a one-bit memory or a fuse technology, wherein the one-bit memory is set, or the fuse is blown, when the sensor 200 first connects to the oximeter 105 through the mating of the cable and sensor connectors, 155 and 160 respectively.

As shown in FIG. 5, the sensor life indicator 210 remains an integral part of the sensor 200 and, therefore, may advantageously take any of the forms discussed above with reference to FIGS. 2 and 3. Preferably, the sensor life indicator 210 comprises the LED 310 of FIG. 3.

Figure 6:
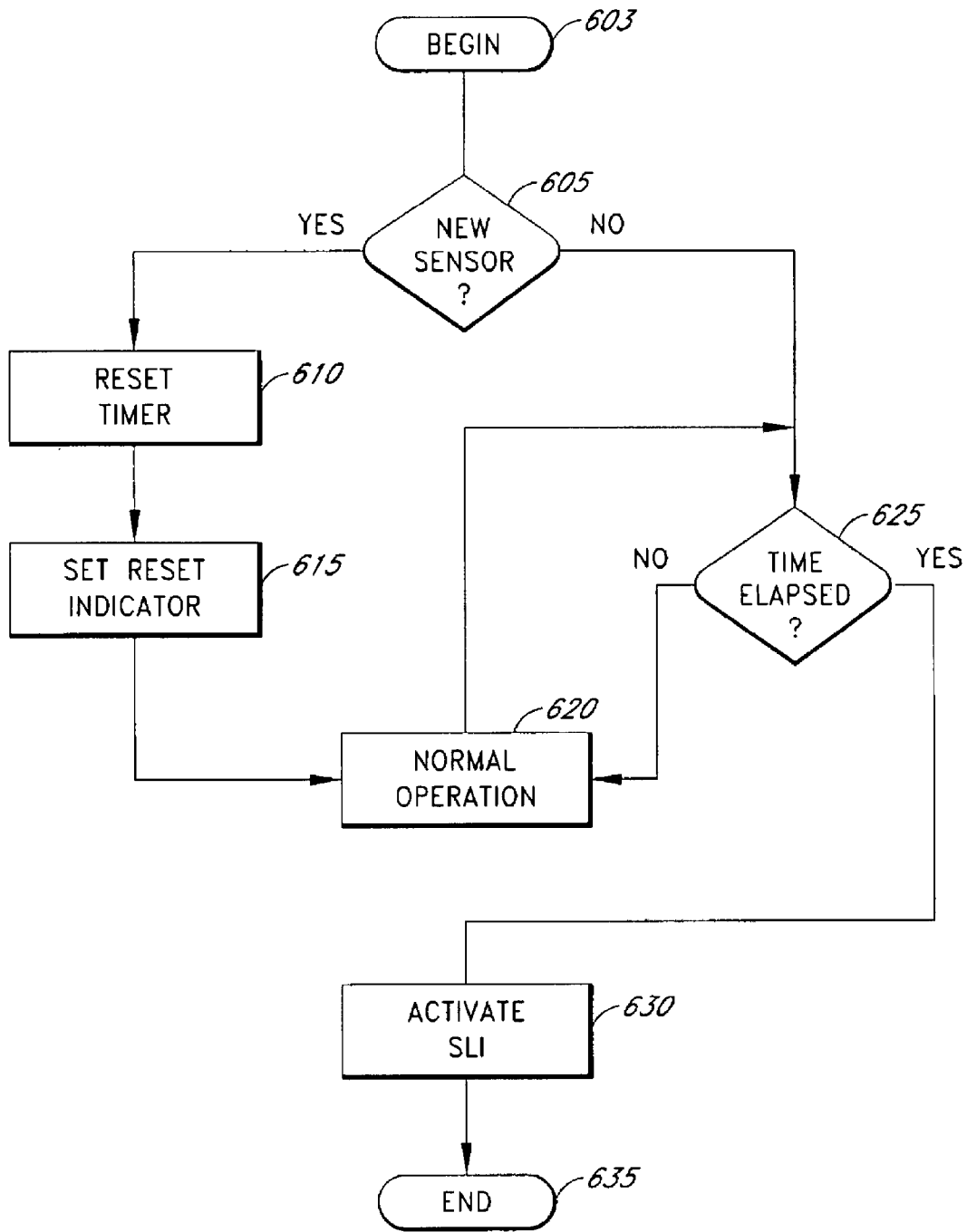
FIG. 6 illustrates a flow diagram of the operation of a microprocessor of the oximetry system of FIG. 5.

FIG. 6 illustrates a flow diagram 600 of the steps taken by the microprocessor 120 of the oximetry system 500 of FIG. 5, according to one embodiment of the invention. As shown in FIG. 6, the process begins when the oximeter 105 is activated to a sensing state by, for example, an operator, in a STEP 603. The oximeter 105 first checks the reset indicator 510, in a STEP 605, to determine whether the sensor 200 has been previously used. If the sensor 200 is new, the microprocessor 120 resets the timer 515, in a STEP 610, and sets the reset indicator 510 on the sensor 200, in a STEP 615. The microprocessor 120 then proceeds with normal operation, e.g., to output a drive signal to the sensor 200, in a STEP 620.

On the other hand, if in the STEP 605, the reset indicator 510 indicates that the sensor 200 has been previously used, or when the sensor 200 is in normal operation, in the STEP 620, the microprocessor 120 checks whether the timer 515 indicates the sensor 200 has reached its predetermined longevity, in a STEP 625. For example, the timer 515 may advantageously compare the number of drive pulses to a predetermined number to conclude whether the sensor 200 has expired.

If the sensor 200 has not expired, the microprocessor 120 again proceeds with normal operation, in the STEP 620. On the other hand, if the timer 515 indicates that the sensor 200 has expired, the microprocessor 120 activates the sensor life indicator 210, in a STEP 630, and then the process terminates, in a STEP 635.

One having ordinary skill in the art will understand that the microprocessor 120 may employ an interrupt driven mechanism for the timer 515. For example, during normal operation, the microprocessor 120 may not continually, or periodically, check the timer 515, as in the STEP 625. Rather, the microprocessor 120 may continually send drive pulses until the timer 515 generates an interrupt that instructs the microprocessor 120 to activate the sensor life indicator 210. A skilled artisan will appreciate that there are a wide number of mechanisms for generating microprocessor interrupts.

Figure 7:
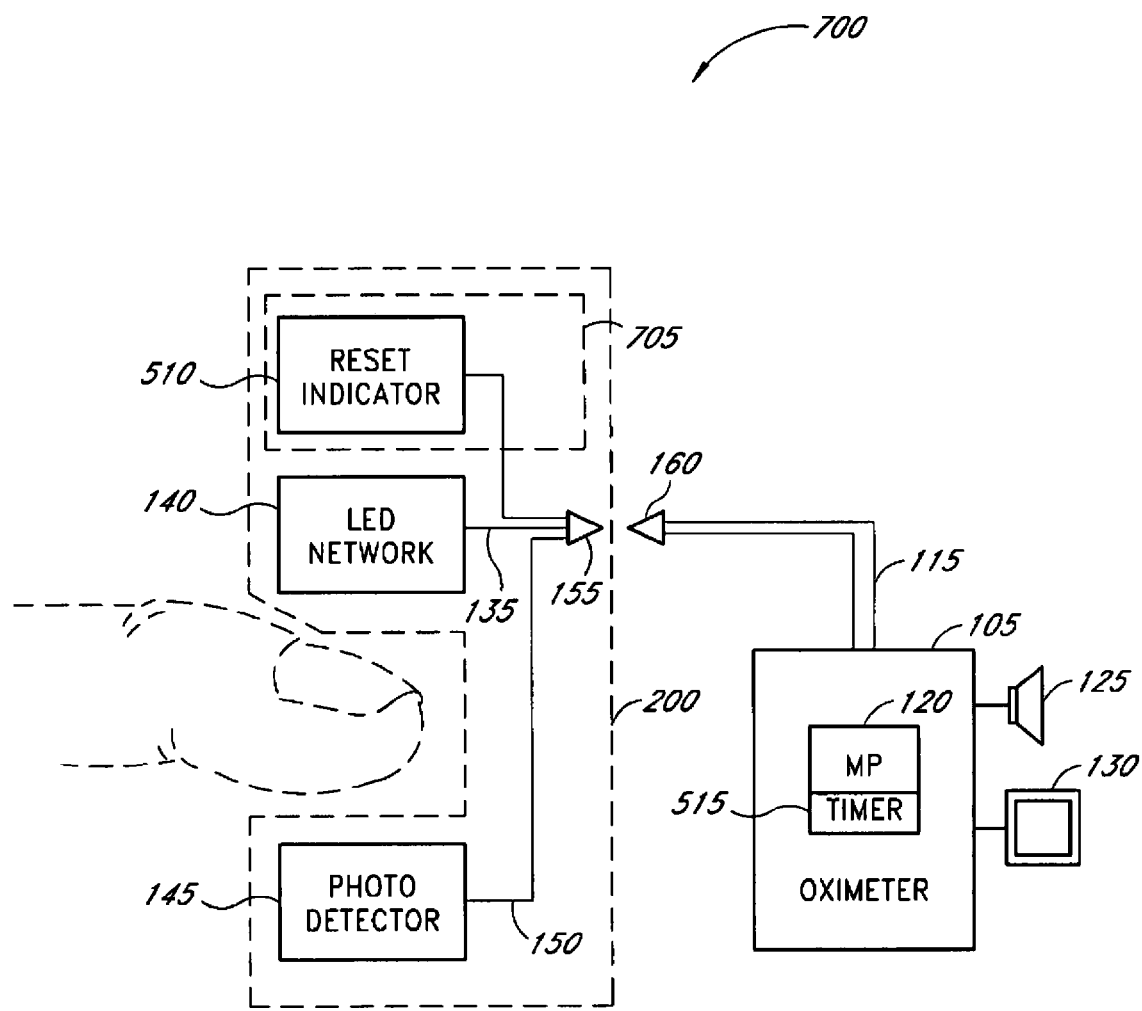
FIG. 7 illustrates a block diagram of an oximetry system having a sensor life monitoring system, according to yet another embodiment of the invention.

FIG. 7 illustrates a block diagram of yet another embodiment of an oximetry system 700 including a sensor life monitoring system 705. According to this embodiment, the oximetry system 700 is similar to that described in reference to FIG. 5. Like FIG. 5, the microprocessor 120 of the oximeter 105 includes the timer 515, or timer-like functions. Also, the sensor life monitoring system 705 advantageously employs the reset indicator 510 to ensure replacement of new sensors when the sensor 200 expires. Moreover, like FIG. 4, the oximetry system 700 employs the oximeter 105 to provide an expiration indication once the sensor 200 expires.

Thus, according to one embodiment, the microprocessor 120 of the oximeter 105 checks the reset indicator 510 to ensure the sensor 200 has not previously been used. Then, the microprocessor 120 drives the LED network 140 and tracks the timing functions. When the predetermined number of drive pulses is reached, the microprocessor 120 employs various mechanisms on the oximeter 105 to generate the expiration indication. For example, the microprocessor 120 may use the speaker 125 or the display 130, even power down the oximeter 105, or the like, to create the expiration indication.

Figure 8:
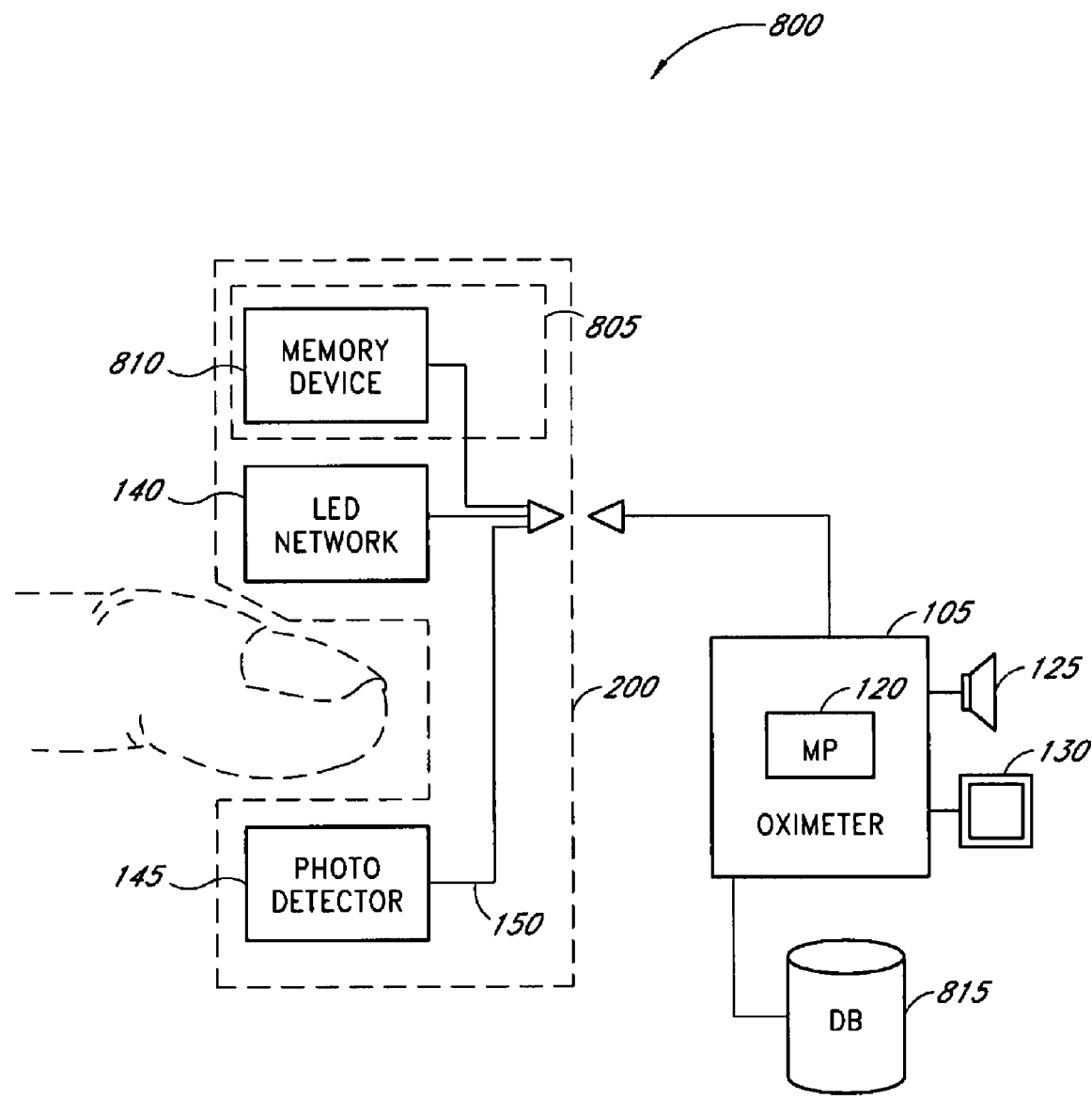
FIG. 8 illustrates a block diagram of an oximetry system having a sensor life monitoring system, according to yet another embodiment of the invention.

FIG. 8 illustrates a block diagram of yet another embodiment of an oximetry system 800. According to this embodiment, the oximetry system 800 includes a sensor life monitoring system 805 having a memory device 810. The memory device 810 is preferably a single wire memory device having a unique identifier, such as memory devices commercially available from companies such as Dallas Semiconductor Corporation. For example, Dallas Semiconductor's DS2401 includes a unique, 64-bit identification number. In this way, the memory device 810 can uniquely identify the sensor 200 from all other sensors.

The oximetry system 800 further includes the microprocessor 120 of the oximeter 105 connected to a memory, such as a database 815. According to the preferred embodiment, the database 815 is stored locally in the memory of the oximeter 105. The oximeter 105 reads the unique identifier from the memory device 810 on the sensor 200 and, if necessary, creates a record in the database 815 corresponding to the unique identifier. Then, as the sensor 200 is used, the oximeter 105 accesses the record corresponding to the unique identifier so as to update the information relating to the longevity of the sensor 200. This information may advantageously include timing information, such as a decremented or incremented chronological count. The information may also, or alternatively, include the number of times the sensor 200 has been used, the number of drive signals the sensor 200 has received, or other similar methods of determining the amount of use for the particular sensor 200 having the particular unique identifier.

According to this embodiment, when the information stored in the database 815 reaches a predetermined threshold for a particular unique identifier, the oximeter 105 advantageously produces the expiration indication in a similar manner to that described in reference to FIG. 4. For example, the oximeter 105 may issue the expiration indication by employing an audio alarm through the speaker 125, a visual alarm through the display 130, or a power-down function that renders the oximeter 105 inoperable. These expiration indications may advantageously continue until the sensor 200 having the unique identifier is replaced with one having a different unique identifier.

Although the database 815 is described as being stored in memory associated with the oximeter 105, the invention is not meant to be limited thereby. Rather, a skilled artisan would recognize that the database 815 may advantageously be stored in a central location, such a remote server connected through a wide number of known technologies, such as a local or wide area network, the internet, or other communications connection. In this way, a monitoring authority, ranging from a pair of pulse oximeters, to one or a number of hospitals, to a particular sensor manufacturer, and the like, can monitor the useful life of sensors identified through their unique identifier stored in the memory device 810.

As an alternative to, or in addition to, the foregoing embodiment where the memory device 810 includes a unique identifier, the memory device 810 may include the ability to store data. Again, such memory devices are commercially available from, for example, Dallas Semiconductor Corporation, and typically allow for read/write access over a single wire. For example, Dallas Semiconductor's DS2502 has the ability to accept new data for non-volatile storage.

According to this embodiment, the oximeter 105 reads data stored in the memory device 810 relating to longevity, and updates that data according to use. For example, the oximeter 105 may read the memory device 810 of sensor 200 and determine that the sensor 200 has been in use for one increment of time, such as one minute. After the sensor 200 has been used for another increment of time, such as another minute as measured by the oximeter 105, the oximeter may write to the memory device 810 such that the memory device 810 now reflects that the sensor 200 has been used for two minutes. This periodic read and write to the memory device 810 continues until the memory device 810 reflects a longevity measurement greater than a predetermined threshold. At that time, the oximeter 105 may advantageously issue the foregoing expiration indication.

A skilled artisan would recognize that a wide variety of timing schemes may be implemented using the foregoing read/write technique. For example, the oximeter 105 may advantageously decrement from a predetermined threshold stored in the memory device 810. On the other hand, the memory device may store the number of times the sensor 200 has been used, the number of drive signals the sensor 200 has received, or other similar methods of determining the amount of use for the particular sensor 200.

Moreover, a skilled artisan would recognize that the foregoing embodiments may advantageously be combined such that the memory device 810 includes both the unique identifier and the ability to store other data. This other data may advantageously include the foregoing read/write timing data, manufacturing data such as sensor type, manufacturing source indication, tolerance levels, operating characteristics, and the like.

Although the foregoing invention has been described in terms of certain preferred embodiments, other embodiments will be apparent to those of ordinary skill in the art. For example, a skilled artisan will recognize the distinction in the foregoing embodiments between those components described as being integral with the sensor 200, or on-sensor components, and those components described as not being integral with the sensor 200, or off-sensor components. The on-sensor components may advantageously be housed in the disposable, reusable, or combination sensors. With respect to the combination sensors, the on-sensor components may be advantageously housed in the disposable portion, the reusable portion, or both portions, of the combination sensor.

Further, the off-sensor components may be housed in any of the longer lasting components associated with the oximeter 105. For example, the off-sensor components may be advantageously located on the sensor connector 160 or on the patient cable 115 where they are readily seen, heard, or felt by the operator or patient.

Moreover, the foregoing embodiments incorporating the memory device 810 of FIG. 8 may advantageously be combined with those embodiments describing the sensor life indicator 210 housed on the sensor 200. In such embodiment, the oximeter 105 may advantageously provide the expiration indication to the sensor life indicator 210 when the oximeter 105 determines that the sensor 200 had expired.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A method of determining an amount of use of a medical sensor capable of communicating signals indicative of physiological parameters of a patient to a medical monitoring device, the method comprising:

monitoring transitions from a medical monitoring device, said transitions usable to activate one or more light sources of a medical sensor, said light sources configured to irradiate tissue of a monitored patient;

applying a sensor life formula to at least the transitions to determine a cumulative use indication indicative of an amount of use of the medical sensor;

storing data related to said sensor life formula in a memory;

when said use indication is above a threshold, indicating to a caregiver that at least a portion of said medical sensor has expired.

2. The method of claim 1, wherein said medical sensor comprises a noninvasive optical sensor.

3. The method of claim 2, wherein said optical sensor includes reusable and disposable components.

4. The method of claim 1, wherein said memory is a component of said optical sensor.

5. The method of claim 1, wherein said memory is a component of a patient monitor.

6. A system for monitoring medical device use, the system comprising:

one or more memories storing one or more cumulative use parameters responsive to a cumulative use of a medical device, at least one of said one or more parameters includes a count indicative of transitions of an emitter drive signal; and a processor configured to use a useful-life formula using the one or more cumulative use parameters, configured to calculate a cumulative use indication indicative of the use of the medical device, configured to determine whether said use indication is above a use threshold, and when said use indication is above said threshold, configured to indicate to a caregiver that at least a portion of said medical device has expired.

7. The system of 6, wherein said medical device comprises an optical sensor configured to output signals indicative of one or more physiological parameters of a monitored patient.

8. The system of 7, wherein said optical sensor includes reusable and disposable components.

9. The system of 7, wherein said optical sensor comprises said memory.

10. The system of 7, comprising a patient monitor, said patient monitor comprising said memory.

* * * * *